United States Patent [19]

Holzner et al.

[11] Patent Number: 5,420,104
[45] Date of Patent: May 30, 1995

[54] PERFUMED COMPOSITION

[75] Inventors: Günter Holzner, Grand-Lancy; Franz Buchli, Thonex, both of Switzerland

[73] Assignee: Firmenich S.A., Geneva, Switzerland

[21] Appl. No.: 193,206

[22] PCT Filed: Jun. 16, 1993

[86] PCT No.: PCT/EP93/01366
§ 371 Date: Feb. 14, 1994
§ 102(e) Date: Feb. 14, 1994

[87] PCT Pub. No.: WO93/25185
PCT Pub. Date: Dec. 23, 1993

[30] Foreign Application Priority Data

Jun. 16, 1992 [CH] Switzerland .................... 1889/92

[51] Int. Cl.$^6$ ................................. A61K 7/46
[52] U.S. Cl. ..................... 512/2; 252/174.11; 252/86; 424/76.4; 424/65
[58] Field of Search ............ 512/2, 3; 252/174.11, 252/8.6; 424/65, 76.4

[56] References Cited

U.S. PATENT DOCUMENTS

| | | | |
|---|---|---|---|
| 4,174,296 | 11/1979 | Kass | 252/312 |
| 4,217,250 | 8/1980 | Holzner | 512/2 |
| 4,803,195 | 2/1989 | Holzner | 512/4 |
| 5,079,227 | 1/1992 | Handjani et al. | 512/2 |
| 5,246,918 | 9/1993 | Behan et al. | 512/3 |
| 5,283,056 | 2/1994 | Chung et al. | 512/2 |

FOREIGN PATENT DOCUMENTS

| | | |
|---|---|---|
| 2008556 | 8/1990 | Canada . |
| 2032105 | 6/1991 | Canada . |
| 0279328B1 | 8/1988 | European Pat. Off. . |
| 0347306 | 12/1989 | European Pat. Off. . |
| 0384034 | 8/1990 | European Pat. Off. . |
| 0433132A1 | 6/1991 | European Pat. Off. . |
| 0451889A1 | 10/1991 | European Pat. Off. . |
| 58-88308 | 5/1983 | Japan . |
| 2013609 | 8/1979 | United Kingdom . |

OTHER PUBLICATIONS

Aerosol Report, vol. 25, No. Jul. 8, 1986, "The Examination of the Effectiveness of Body Deodorant Sprays" by Günter W. Holzner.

Primary Examiner—James H. Reamer
Attorney, Agent, or Firm—Pennie & Edmonds

[57] ABSTRACT

A perfumed composition is described containing a cationic phospholipid, a perfume base having microbial action, and a fatty alcohol having 10 to 22 carbon atoms, extremely useful in deodorants and antiperspirants. Its anti-microbial activity is greater than that of known compositions, and can be measured by the direct spray method using the device shown in the FIGURE.

20 Claims, 1 Drawing Sheet

PERFUMED COMPOSITION

TECHNICAL FIELD AND PRIOR ART

The present invention relates to the perfume and cosmetic industry and, more particularly, to that of the body deodorants and antiperspirants.

The main function of a body deodorant or antiperspirant is that of preventing body malodor due to the bacterial decomposition and to the oxidation of the organic substances which make up the sweat. Conventionally, deodorants contain substances which are capable of masking this body malodor and of inhibiting the proliferation of the bacteria responsible for the deterioration of sweat, whereas antiperspirants comprise components which reduce perspiration while having a bactericidal activity.

In both instances, there is at present a tendency from the consumer to prefer deodorant products based on natural or nature identical (i.e., based on substances which are synthesized but the structure of which is identical to that of naturally occurring compounds) active principles. To satisfy this demand, one seeks to suppress in the body deodorants and antiperspirants the conventional bactericidal, bacteriostatic and antiperspirant substances, which are often allergenic, and to replace them by natural active principles. Thus, one has observed in the last few years the development of products whose bactericidal action is due essentially to the presence of perfuming compositions containing carefully selected perfuming ingredients, so as to ensure an adequate deodorising action without resorting to the classical bactericidal substances [see for example, G. W. Holzner in Aerosol Report 25, 354 (1986); see also published patent application EP 451 889 which contains quite a complete analysis of the art knowledge in the field of the bactericidal activity of synthetic or natural origin perfuming ingredients].

Another particular example of a composition representing this tendency is that of the compositions described in European patent application N° 433 132, which comprise essential oils having an anti-bacterial and/or an anti-fungus activity dispersed in an aqueous phase stabilised by means of a lipid phase which comprises anionic and non-ionic amphiphile lipids.

On the other hand, a choice body deodorant must present as large a spectrum of bactericide activity as possible, i.e., it must prevent, as efficiently as possible, the growth of all the microbial organisms present on the skin. However, it is well known that the deodorant products based on perfuming substances do not have the same efficiency against all these varieties of organisms.

The aim of the present invention is to bring an original contribution to the solution of this problem.

DESCRIPTION OF THE INVENTION

The invention relates to a perfuming composition characterized in that it contains a cationic phospholipid, a perfuming base having antimicrobial activity ("PBAA") and a fatty alcohol having from 10 to 22 carbon atoms.

We have in fact discovered that the simultaneous presence of these three ingredients in the perfuming composition made it possible to inhibit the action of a great variety of microorganisms and imparted to said composition a remarkable deodorant power which rendered it particularly convenient for application in deodorant and antiperspirant articles, as it can be seen from the examples presented further on. It was surprisingly observed that the presence of the "PBAA" and of the fatty alcohol reinforced, in a synergic manner, the action of the cationic phospholipids and made it possible to obtain improved perfuming compositions, relative to the prior art ones.

Furthermore, we have also observed that the compositions according to the invention could have a considerable antiperspirant effect, even without resorting to the use of aluminium or aluminium and zirconium salts, currently used as active antiperspirant substances.

The cationic phospholipids are nature identical substances which are commonly used in cosmetics as emulsifiers or emollients. However, to our knowledge, there is no description in the literature concerning the use of these substances in body deodorants or antiperspirants. Yet, we have now discovered that the perfumed compositions according to a preferred embodiment of the invention, characterized in that they present an antimicrobial activity of at least 80%, as measured by the direct spray method described hereinafter, effectively inhibit the malodor of perspiration during at least twelve hours, when applied on the skin, and make it possible to avoid the use of substances such as hexachlorophene, dichlorophenol, trichlorosalycilanilide, tribromosalycilanilide (TBS), tetrachlorosalycilanilide (TCSA), trichlorocarbanilide (TCC) or Irgasan ® DP-300 (Ciba-Geigy), currently used up until now as bactericide or bacteriostatic agents.

The compositions of the invention have definite advantages over the deodorant and antiperspirant compositions which make use of the conventional active principles. In fact, the cationic phospholipids are non-toxic biodegradable substances, which do not provoke irritating effects on the skin, but, on the contrary, have a softening effect on the latter.

According to a preferred embodiment of the invention, there can be used synthetic origin phospholipids, namely nature identical ones. We observed that better results were obtained when using phospholipids of the formula

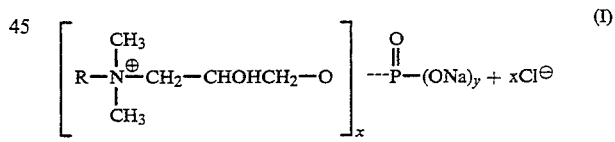

wherein R is a linoleamidopropyl or a cocamidopropyl radical and $x+y=3$.

Such phospholipids can be found on the market, namely under the commercial names of Phospholipid PTC and Phospholipid EFA (Mona Industries Inc., USA).

These phospholipids can be directly added to the classical formulations of currently used deodorant or antiperspirant bases. Examples of such preparations are presented further on. Preferably, the phospholipids are added in concentrations comprised between 0.05 and 5% by weight, relative to the weight of the perfumed composition into which they are incorporated.

As fatty alcohol present in the perfumed compositions according to the invention, there will be preferably used a fatty alcohol having from 14 to 18 carbon atoms. Cetyl and myristyl alcohols revealed themselves to be particularly advantageous for this application.

According to a preferred embodiment, the fatty alcohol is added in a concentration comprised between 0.02 and 2% by weight, relative to the weight of the perfumed composition.

The perfuming base with antimicrobial action, or "PBAA", on the other hand, will be preferably added in a concentration comprised between 0.1 and 5% by weight, relative to the weight of the composition.

According to a preferred embodiment, the perfumed composition according to the invention contains about 0.05 to 2% by weight of phospholipid, about 0.5 to 5% by weight of "PBAA" and about 0.05 to 2% by weight of fatty alcohol, relative to the weight of composition, and presents an antimicrobial activity of at least 90%, as measured by the direct spray method.

By "perfuming base with antimicrobial activity" ("PBAA") it is understood here a perfuming base formed of a mixture of perfuming substances, on their own or in solution or suspension in their usual diluents, solvents or coingredients, said substances being chosen in a variety of chemical classes, comprising for example esters, ethers, alcohols, aldehydes, ketones, acetals, nitriles, terpenic hydrocarbons, heterocyclic nitrogen- or sulfur-containing compounds, as well as natural origin essential oils. The choice of these perfuming ingredients will be dictated by the nature of the olfactive effect one desires to achieve, as well as by the required global antimicrobial activity of the cited perfuming base.

According to a preferred embodiment of the invention, the "PBAA" will present an antimicrobial activity of at least 60% as measured by the direct spray method described hereinafter. It should be noted however, that these values of antimicrobial activity are purely indicative, since other bases having a lower microbial activity may well turn out to be perfectly adequate for use in the perfumed compositions of the invention.

Thus, more generally, the "PBAA" can be defined as a perfuming base which contains a preponderant amount, preferably 60% or more by weight, of perfuming ingredients known to possess antimicrobial action. The latter need not be enumerated here in an exhaustive manner. In fact, there are many examples of such ingredients in the prior art (see, for example, EP 451 889 and the references there cited) and the man in the art is nowadays able to choose them so as to harmonize the olfactive effect that he seeks, which is also imparted by said perfuming base, and the requirement of antimicrobial action of the latter, determined by the proportion of these ingredients relative to that of the ingredients whose action is purely olfactive.

Moreover, we have also established, according to the invention, that the perfuming ingredients whose antimicrobial activity is at least 60%, as measured by the direct spray method described further on, could also be advantageously used as perfuming ingredients with antimicrobial action in the "PBAA" above-mentioned. Thus, the invention has also as its object a "PBAA", characterized in that it contains at least 60% by weight, relative to the weight of the base, of perfuming ingredients whose antimicrobial activity is at least 60%, as measured by the direct spray method and the perfumed compositions which contain this "PBAA" are preferred embodiments of the invention.

As previously cited, the "PBAA" also fulfills the function of imparting to the perfumed compositions according to the invention the desired odor notes. Thus, it will also contain perfuming ingredients of current use the effect of which is mainly olfactive and which, like the above-mentioned microbicidal perfuming ingredients, can be selected in the chemical classes already cited above. The choice of these ingredients will depend on the desired olfactive effect and on the nature of the product to be perfumed, as well as, of course on the taste of the creating perfumer.

The "PBAA" present in the perfumed compositions according to the invention can be added to the latter as such or in microencapsulated form, or yet in the form of emulsions such as those described in European patent N° 279 328 or in European patent application N° 384 034. The information contained in these documents which relates to the content or to the preparation of said emulsions, or to the microencapsulation of perfuming bases by means of the method there described, are hereby included by reference.

The "PBAA" will be added to the perfumed compositions according to the invention in the concentrations usual in the art. The values of these concentrations depend on the nature of the deodorant or antiperspirant end product, as well as on the desired odor effect, and the skilled person is quite capable of choosing them as a function of these parameters. Preferred concentrations have already been cited above.

The perfumed compositions of the invention may also contain plant extracts rich in flavonoids. These are plant extracts soluble in water or ethanol and which no longer contain essential oils, the latter having been prior extracted by steam distillation. The anti-oxidizing action of these extracts reinforces the deodorant power of the composition.

Plant extracts from a wide variety of plants such as rosemary, sage, lavender and lavandin, thyme, green tea, oregano, coriander and laurel, can also be used to this effect. Extracts from the leaves and fruits of the olive tree or from the eucalyptus, as well as from the leaves and rinds of the fruits of the orange and lemon trees and other citrus trees, can also be used. Particularly advantageous results were obtained with rosemary extracts, amongst which one can cite by way of example the commercial product from FIS (Food Ingredients and Specialities S.A., Vevey, Switzerland) known under the name of Spice Extract AR.

These plant extracts will be added to the composition generally in the form of water or ethanol solutions, in concentrations of the order of 0.05 to 0.5% by weight, relative to the weight of the composition into which they are incorporated. When the perfuming base is used in microencapsulated form, for example, as described in EP 279 328 or EP 384 034, the plant extract can be incorporated in the encapsulating emulsion.

The perfumed composition according to the invention can still contain other substances such as hydrocolloids. These are natural or synthetic polymeric substances, such as carboxymethylcellulose, hydrosoluble proteins, certain plant resins like gum arabic, alginates and carragenans. The use of polyvinylpirrolidone or of its quaternary derivatives has also revealed itself advantageous, reinforcing the antimicrobial effect of the composition.

Although the composition according to the invention makes it possible to avoid using conventional bactericide and antiperspirant agents, it goes without saying that, if wished, such agents can be added thereto. The concentrations in which these agents are added will then be typically lower than the usual concentrations, namely in what concerns the bactericide and bacteriostatic agents.

The perfumed composition according to the invention is particularly convenient for the preparation of various articles intended for body care. These articles may present themselves in a variety of different forms such as soaps, sticks, roll-ons, aerosols or mechanical or manual pressure vaporizers. Depending on the nature of these articles, the composition may be used as such, in the form of an ethanol solution, eventually admixed to an aerosol propellent, or yet in admixture with ingredients of varied nature currently used in these articles and illustrated in the examples presented further on.

These deodorant or antiperspirant articles according to the invention are obtained by mixing their different ingredients by means of conventional equipment. The mixing technique is itself known and any detailed description thereof is not warranted here. Detailed examples are given further on.

Furthermore, we have also discovered that the perfumed composition according to the invention had a much wider application and that it could namely be advantageously used in detergents and fabric softeners. It was in fact observed that textiles treated with these products had a substantial deodorant action when carried on the skin. In addition, it has been found that the combination of the cationic phospholipids with cetyl or myristyl alcohol had a softening action on the textiles and thus made it possible to reduce, or even eliminate, the use of quartenary tensioactive agents such as stearyl dimethylammonium chloride, currently used for this softening effect.

It was also observed that these two ingredients and, in particular the phospholipid, exhalted the perfuming effect of the "PBAA", such that the odor effect on the textiles was much stronger and tenacious, thus much longer-lasting, then when the "PBAA" was used on its own to perfume the detergent or fabric softener.

The direct spray method, or "DSM", described by G. Holzner in the previously cited reference, allows the determination of the bactericide or antimicrobial effectiveness of cosmetic preparations applied on the skin.

Thanks to a dosing aerosol valve, the ready-to-use deodorant or antiperspirant composition, or a corresponding solution of the active materials, is directly sprayed on the surface of the nutritive gel prior infected with the desired germ. The latter is then incubated at 37° C. during 24 or 48 hours, in view of subsequent evaluation of the bacteria on the treated circular area. The antimicrobial action of the perfumed composition is then defined by evaluating the area of the zone free of bacteria, relative to the total circular area treated. We have observed that the perfumed compositions according to the invention had a good deodorant activity when the ratio of the two areas was of about 80% or more, upon treating the nutritive gel inoculated with germs with said composition or its active principle.

With reference to the FIGURE, the 50 ml glass aerosol flask (1), equipped with a dosing valve (2) having a 0.4 mm diffuser on the outlet, is placed on a fixing device (3) above a Petri plate (4), such that the outlet of the valve is 9 cm above the surface of the plate. Under these conditions, there is formed a spray cone which marks on the Agar plate a circular surface of about 3 cm diameter. The Petri plate is typically in plastic material or in glass and has a diameter of 9 cm.

One uses a conventional Petri plate, available on the market and already carrying the nutritive gel. By means of a Pasteur pipette, one places ten drops of culture broth (already inoculated with the wanted germ or germs and incubated during 48 h at 37° C.) on the Agar plate and spreads them uniformly on the latter by means of a glass spatula. This is incubated for 2 h at 37° C. and the plate is put on the fixing device (3).

Typically, to measure the antimicrobial activity of the perfumed composition according to the invention, one proceeds as follows.

Upon the testing of aerosol products, the perfumed composition and the propellent, for example in the respective proportions of 40 and 60%, are placed in the flask (1). If one was dealing with compositions intended for use in deodorant or antiperspirant sticks, their active materials, in the respective application proportions, were dissolved in 95% ethanol and the resulting solution placed in the flask with the propellent as described before. The dosing valve was then installed in a manner known in itself, taking care that the extremity of the plunging tube reaches the bottom of the flask. The latter was placed on the fixing device in such a way that the opening of the valve is made to point in the direction of Petri plate. The latter was sprayed with active solution, through a single activation of the valve. The surface of the plate thus sprayed was measured and then incubated at 37° during 24 to 48 h. After incubation, the area of the zone of the plate which is exempt of bacteria was measured and the antimicrobial activity of the perfumed composition according to the invention was thus defined.

A blank solution composed generally of 95% ethanol was always sprayed on Petri plates under the same conditions, for controlling purposes.

In this method there were used the following germ cultures:

*Staphylococcus epidermidis*
*Staphylococcus aureus*
*Escherichia coli*
*Pseudomonas aeruginosa*
*Candida albicans*
*Corynebacterium pseudodiphteriae*

This is a group which includes the organisms most currently encountered on the skin.

As previously said, it is well-known that, in order for a deodorant composition to have an effective action against perspiration malodor, it must have bactericide activity against as large a spectrum of germs as possible and, in any case, including those cited above. We have now established that the compositions according to the invention effectively inhibit the action of all these microorganisms.

It is clear that the method described above can also be used to determine the antibacterial activity of the individual ingredients of the perfumed composition according to the invention. In this manner, we have been able to establish that perfumed compositions conforming to the invention could also be obtained when they contained, in addition to the cationic phospholipid and the fatty acid, a perfuming base, said base presenting a certain individual antimicrobial activity, such as measured by the direct spray method. This activity is then measured under the conditions previously described, using a solution of the "PBAA" in ethanol as the spraying solution. Of course, the "PBAA" is present in this solution in the same weight proportions as in the perfumed compositions according to the invention.

The antimicrobial activity of the perfuming ingredients intended to be incorporated in the perfuming base with antimicrobial activity, or "PBAA", can also be measured under the conditions previously described, but using as spraying solution a solution of the perfuming ingredient in ethanol, solution wherein said perfuming ingredient is used in the same concentration as in said "PBAA".

The invention will be described in more detail by way of the examples presented hereinafter.

after, wherein are also indicated the antimicrobial activities of the compositions according to Examples 2, 5 and 6.

TABLE I

| Composition | Staphylococcus epidermidis | Staphylococcus aureus | Escherichia coli | Pseudomonas aerginosa | Candida albicans | Corynebacterium pseudodiphteriae |
|---|---|---|---|---|---|---|
| Perfuming base acc. to example 1 | ** | ** | + | * | ** | ** |
| Comp. 1 acc. to example 2 | ** | ** | ** | * | ** | ** |
| Composition acc. to example 5 | ** | ** | ** | * | ** | ** |
| Composition acc.to example 6 | ** | ** | ** | * | ** | ** |

+ antimicrobial activity above 70%, as measured by the DSM
*antimicrobial activity above 80%, as measured by the DSM
**antimicrobial activity above 90%, as measured by the DSM

BRIEF DESCRIPTION OF THE DRAWING

The single FIGURE is a perspective view of the device used in the direct spray method ("DSM").

MODES OF CARRYING OUT THE INVENTION

EXAMPLE 1

Perfuming Base With Antimicrobial Action ("PBAA")

Figure 1:
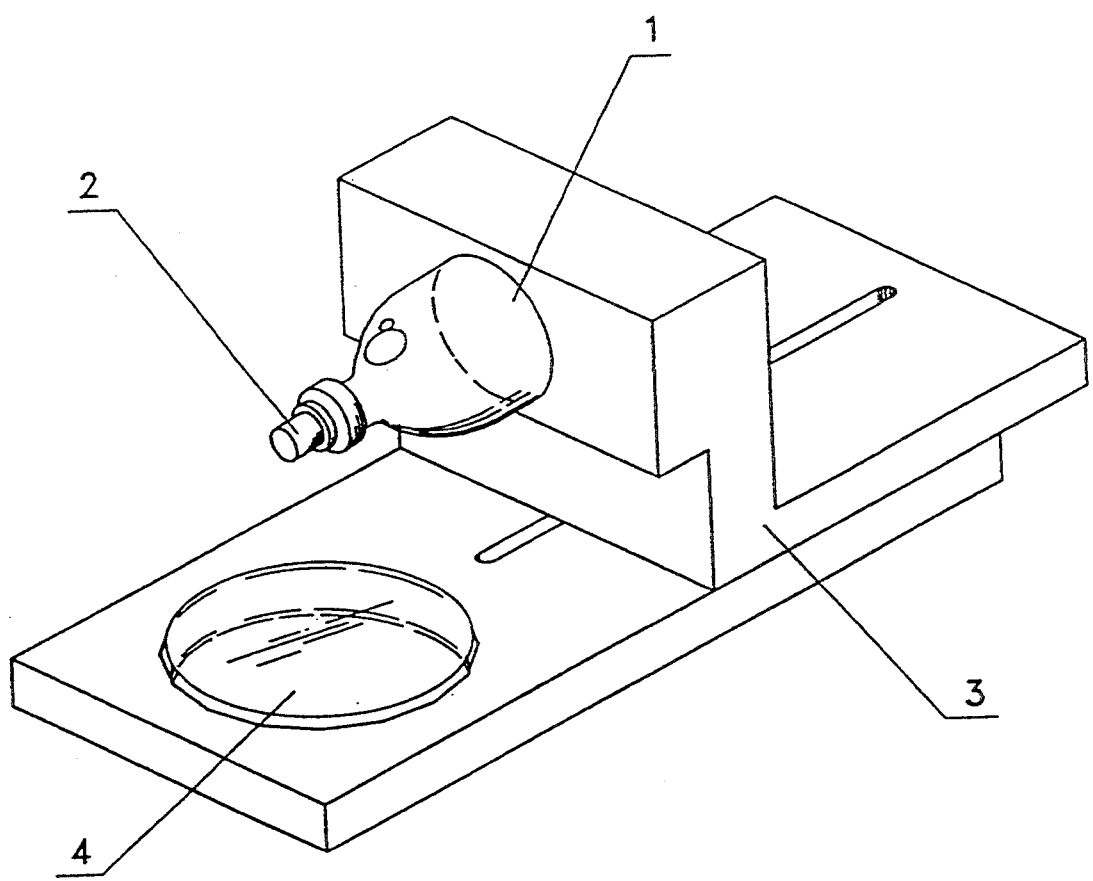

A perfuming base with bactericide action was prepared by mixing the following ingredients:

| Ingredients | Parts by weight |
|---|---|
| Benzyl acetate | 10.7 |
| Cyclohexyl acetate* | 5.0 |
| Styrallyl acetate* | 1.5 |
| Octanol* | 0.3 |
| Decanol* | 3.0 |
| Amylcinnamic aldehyde | 4.0 |
| 10% Ambrox ® DL[1] in DIPG | 0.5 |
| Brazil rosewood oil* | 10.0 |
| Morocco camomile oil* | 2.5 |
| Allyl caproate* | 3.0 |
| Delphone[2]* | 5.0 |
| Orange leaves absolute* | 1.5 |
| Geraniol* | 8.0 |
| Madagascar clove oil* | 5.0 |
| Bourbon geranium oil* | 4.0 |
| Hedione ® [3]* | 10.0 |
| Hydroxycitronellal | 2.5 |
| Iralia ® [4] | 1.5 |
| Synth. jasmin absolute | 12.0 |
| Wardia ® [5] | 6.0 |
| Synth. Ylang oil.* | 4.0 |
| Total | 100.0 |

*Perfuming ingredients presenting an antimicrobial action above 70% (when diluted in ethanol at a concentration of 0.5%), as measured by the direct spray method.
[1] tetramethyl perhydronaphthofuran; origin: Firmenich SA, Geneva, Switzerland
[2] pentyl cyclopentanone; origin: Firmenich SA, Geneva, Switzerland
[3] methyl dihydrojasmonate; origin: Firmenich SA, Geneva, Switzerland
[4] methylionone (isomer mixture); origin: Firmenich SA, Geneva, Switzerland
[5] origin: Firmenich SA, Geneva, Switzerland This perfuming base, in solution in ethanol at a concentration of 1.5%, showed an average antimicrobial activity above 80%, as measured by the direct spray method, as can be seen from the Table presented herein-

EXAMPLE 2

Perfumed Composition for Pressure Spray

A perfumed composition with deodorising action, intended to be used by means of an application device comprising a mechanical or manual pressure spray system ("pumpspray" or "squeeze bottle") was prepared by means of the following ingredients:

| Ingredients | Composition 1 | Composition 2 |
|---|---|---|
| | (% by weight) | |
| Klucel EF[1] | — | 0.3 |
| Water | 22.0 | 20.9 |
| Luviquat Mono CP[2] | — | 0.2 |
| Luviskol K-30[3] | — | 0.4 |
| Gafquat HS-100[4] | — | 0.2 |
| 95% Ethanol | 75.0 | 75.0 |
| Phospholipid EFA[5] | 0.4 | 0.4 |
| Rosemary extract soluble in ethanol | 0.2 | 0.2 |
| Myristyl alcohol | 0.2 | 0.2 |
| Chremophor RH 40[6] | 0.7 | 0.7 |
| Perfume[7] | 1.3 | 1.3 |
| Tenox GT II[8] | 0.2 | 0.2 |
| Total | 100.0 | 100.0 |

[1] hydroxypropylcellulose; origin: Hercules Co., USA
[2] hydroxyethyl cetyldimonium phosphate; origin: BASF AG, Germany
[3] polyvinylpyrrolidone; origin: BASF AG, Germany
[4] polyquaternium 28; origin: GAF Corp., USA
[5] linoleamidopropyl PG-dimonium chloride phosphate; origin: MONA Ind., USA
[6] hydrogenated and ethoxylated castor oil; origin: BASF AG, Germany
[7] Evasion 111.092, citrus, spicy type, antimicrobial activity above 70%; origin: Firmenich SA, Geneva
[8] tocopherol; origin: Eastman Chemicals, USA The above-mentioned ingredients were mixed according to current methods in the art and poured into spray containers. Composition 2 comprises the same active principle as composition 1, in the form of an encapsulating emulsion of the type of those described in EP 384 034.

The average antimicrobial activity of composition 1, measured by the direct spray method, was above 90% as can be seen in Table 1.

EXAMPLE 3

Perfumed Composition for Roll-On

A perfumed composition with antiperspirant action, intended to be incorporated in roll-on type application devices, was prepared with the following ingredients:

| Ingredients | Parts by weight |
| --- | --- |
| Micro Dry Ultrafine[1] | 20.0 |
| Dow Corning 345[2] | 73.3 |
| Anhydrous ethanol | 1.5 |
| Bentone 38[3] | 2.7 |
| Perfume[4] | 0.5 |
| Active base | 2.0 |
| Total | 100.0 |

[1] aluminium hydrochloride; origin: Reheis Chem. Co., USA
[2] cyclomethicone; origin: Dow Chemicals, USA
[3] quaternium 18-hectorite; origin: Rheox Inc., USA
[4] Lixia liquid, aldehydic, floral type; antimicrobial activity above 70%; origin: Firmenich SA, Geneva The above-mentioned ingredients were mixed according to current techniques, the active base having been previously prepared as described hereinafter. The mixture was then poured into roll-on type distributing devices.

Active Base

This base was obtained as described hereinafter, by means of the following ingredients:

| Ingredients | Weight |
| --- | --- |
| Water | 115.000 |
| Tylose H-10[1] | 1.000 |
| Rosemary extract soluble in water | 25.000 |
| Sugar | 1.000 |
| Capsul[2] | 49.175 |
| Hostaphat KL-340[3] | 0.200 |
| Phospholipid EFA[4] | 15.000 |
| Citric acid | 1.000 |
| Aloe 10 X[5] | 10.000 |
| Micronised allantoin[6] | 5.000 |
| Antifoam[7] | 0.100 |
| Perfume[8] | 25.000 |
| BHT[9] | 0.025 |
| Tenox GT II[10] | 2.500 |
| Total | 250.000 |

[1] hydroxyethylcellulose; origin: Höchst AG, Germany
[2] starch Na-octenylsuccinate; origin: National Starch Inc., USA
[3] trilaureth-4-phosphate; Höchst AG, Germany
[4] see example 2
[5] aloe extract; origin: Terry Corp., USA
[6] origin: Chemie Linz, Austria
[7] silicon oil emulsion; origin: Bayer AG, Germany
[8] see above
[9] p-tert-butylhydroxytoluene; origin: Shell Co., Holland
[10] tocopherol; origin: Eastman Chemicals, USA The ingredients of this active base were dissolved one after the other in the order indicated. The resulting emulsion was well homogenised by of a Silverson type mixer, at room temperature.

The emulsion was then heated to 60° C. and spray-dried in a conventional Büchi type spray-drier, the temperature of the inlet air being 220° C. and the temperature of the outlet air, mixed with the powder, being 120° C. There was thus obtained a powder containing all the above-mentioned ingredients, except the water. This powder was formed of hydrosoluble microcapsules containing the perfume.

The powder thus obtained was then incorporated into the perfumed composition, in the proportion indicated.

EXAMPLE 4

Perfumed Composition for Aerosol Spray

A perfumed composition with antiperspirant action, intended to be incorporated in a spray type application device, was prepared by means of the following ingredients:

| Ingredients | Parts by weight |
| --- | --- |
| Micro Dry Ultrafine[1] | 8.0 |
| Dow Corning 345[2] | 19.6 |
| Perfume[3] | 0.4 |
| Active base[4] | 2.0 |
| Propellent propane/butane[5] | 70.0 |
| Total | 100.0 |

[1],[2],[3] and [4] see example 3
[5] 2.5 bar n-mixture

The mixture prepared according to the usual methods was poured into spray aerosol containers.

EXAMPLE 5

Perfumed Composition for Aerosol Spray

A perfumed composition with deodorant action, intended to be applied by means of a spray type device, was prepared by mixing the following ingredients:

| Ingredients | Parts by weight |
| --- | --- |
| Klucel EF[1] | 0.30 |
| Rexene Fe 3 spec.[2] | 0.03 |
| Demineralised water | 5.00 |
| Phospholipid PTC[3] | 0.30 |
| Luviskol K 30[4] | 0.50 |
| Gafquat HS-100[5] | 0.40 |
| 95% Ethanol | 90.17 |
| DL-α-Tocopherol[6] | 0.20 |
| Cetyl alcohol | 1.00 |
| Rosemary extract soluble in ethanol[7] | 0.10 |
| Perfume[8] | 2.00 |
| Total | 100.00 |

[1] see example 2
[2] dihydroxyethyl glycine; origin: Rexolin
[3] cocamidopropyl PG-dimonium chloride phosphate; origin: Mona Ind., USA
[4] see example 2
[5] see example 2
[6] origin: Hoffmann-La Roche, Switzerland
[7] Spice extract AR; origin: FIS, Vevey, Switzerland
[8] perfuming base described in example 1

The above-mentioned ingredients were mixed in such a way as to obtain a perfectly homogeneous mixture. This mixture was poured into an aerosol distribution device with adjunction of dimethylether, in the respective 60:40 proportions.

The average antimicrobial activity of this composition was above 90%, as measured by the direct spray method (see Table 1).

EXAMPLE 6

Perfumed Composition for Aerosol Spray

A perfumed composition with deodorant action, intended to be applied by means of a spray type device, was prepared by mixing the following ingredients:

| Ingredients | Parts by weight |
| --- | --- |
| 95% Ethanol | 96.6 |
| Phospholipid PTC[1] | 0.2 |
| Rosemary extract soluble in ethanol[2] | 0.1 |
| D, L-α-Tocopherol[3] | 0.2 |
| Myristyl alcohol | 1.0 |

-continued

| Ingredients | Parts by weight |
| --- | --- |
| Perfume[4] | 1.9 |
| Total | 100.0 |

1), 2), 3) and 4) see example 5

The mixture of these ingredients was poured into a distributor with the propellent consisting of a 90:10 isobutane/propane mixture. The relative proportions of the active mixture and propellent were 65% and 35% respectively.

The perfumed composition thus obtained had an average antimicrobial activity above 90% against all the organisms previously cited.

EXAMPLE 7

Perfumed Composition for a Soap

A perfumed soap was prepared with the following ingredients:

| | Ingredients | Parts by weight |
| --- | --- | --- |
| I | Soap base[1] | 93.0 |
| II | Perfume[2] | 1.5 |
| | Cetyl alcohol | 0.5 |
| | Phospholipid PTC or EFA[3] | 5.0 |
| | Total | 100.0 |

[1] Prisavon 9250; origin: Unichema
[2] perfuming base according to Example 1
[3] see preceding examples Part II was admixed and slightly heated to obtain a homogeneous emulsion. Parts I and II were then mixed by means of a rolling mill having three rolls. Finally, the paste thus obtained was extruded in an extrusion press and the soap was stamped.

An ethanol solution of the active base of this soap (part II), wherein the three ingredients were used in the proportions indicated, presented an antimicrobial activity close to 100%.

On the other hand, a "Hill Top" type test carried out on a panel of 5 individuals showed that the soap thus prepared presented an average deodorant value of 2.8.

EXAMPLE 8

Perfumed Composition for a Liquid Fabric Softener

A perfumed composition intended to be used in a liquid fabric softener was prepared with the following ingredients:

| | Ingredients | Parts by weight |
| --- | --- | --- |
| I | Perfume | 2.0 |
| II | Phosphohpid PTC[2] | 15.0 |
| | Cetyl or myristyl alcohol | 5.0 |
| III | Demineralised water | 77.8 |
| | Citric acid | 0.2 |
| | Total | 100.0 |

[1] perfuming base according to example 1
[2] see preceding example

Parts II and III were separately heated to 60° C. and part III poured into part II. The mixture was stirred until the temperature reached 40° C. and part I was added, while maintaining stirring until obtaining a homogeneous mixture and until the temperature had decreased to about 20° C.

For application, 30 to 50 g of this emulsion were added to the water of the last rinsing in a fabric washing cycle carried out in a washing machine. Alternatively, the perfumed composition prepared as described above can be added to a currently used liquid softener base.

The fabrics treated with the perfumed composition described above had a substantial deodorant action when worn on the skin.

In addition, and concurrently, another identical batch of fabrics was treated in the same way with a fabric softener containing the same amount of an emulsion wherein part II above had been replaced by a classical quartenary surfactant, i.e., Praepagen WK from Höchst (stearyldimethylammonium chloride).

The two batches of fabrics were evaluated on a blind test by a panel of expert perfumers, which panel observed that the odor of the fabrics treated with the composition according to the present invention was remarkably stronger than the odor of the fabrics treated with the composition containing the classical ingredients, and was also much longer-lasting on the dried fabrics.

EXAMPLE 9

Perfumed Composition for Fabric Softener

A composition intended for a fabric softener to be used in a clothes dryer was prepared with the following ingredients:

| Ingredients | Parts by weight |
| --- | --- |
| Perfume[1] | 15.0 |
| Phospholipid PTC[2] | 40.0 |
| Cetyl alcohol | 34.8 |
| Stearic acid | 20.0 |
| Citric add | 0.2 |
| Total | 100.0 |

1) and 2) see example 7

The ingredients were mixed and the mixture was slightly heated (above 70° C.) to obtain a homogeneous and liquid mixture at this temperature. Tissues of the non-woven type, having 25 cm×25 cm dimension, were then impregnated with 1.5 to 2 g of this mixture. The tissues were added to wet fabrics in an electrical tumble dryer. The fabrics dried in the presence of these tissues were soft and showed a substantial deodorant action when worn on the body.

EXAMPLE 10

In order to test the deodorant power of the perfumed composition according to the invention, a panel of twenty individuals applied on one armpit, by means of an aerosol spray, composition 1 described in example 2, while the other armpit was either not treated, or treated with a blank product containing the same perfume, but using conventional deodorant ingredients. Each individual was then asked to compare, after 8, 12 and 24 hours, the odor of the two armpits and to indicate which armpit developed the more agreeable odor. After one week, the same test was repeated, but interchanging the sprays, such as to eliminate possible effects coming from the fact that, for the same person, the two armpits may present different odors. At the end of the two weeks of tests it was possible to conclude that about 70% of the members of the panel preferred the odor of the armpit treated with the product according to the invention, 25% having found identical odors for the two armpits and the remainder having preferred the odor of the armpit that had been treated with the blank product.

We claim:

1. An antimicrobial perfumed composition comprising concentrations of the following components effective in combination to prevent the formation of perspiration odor: a cationic phospholipid, a perfuming base having antimicrobial activity, a fatty alcohol having from 10 to 22 carbon atoms and a suitable carrier, wherein the perfuming base has an antimicrobial activity of at least 60%, as measured by the direct spray method.

2. A composition according to claim 1, wherein the antimicrobial activity is at least 80%, as measured by the direct spray method.

3. A composition according to claim 1, wherein the cationic phospholipid is a compound of formula

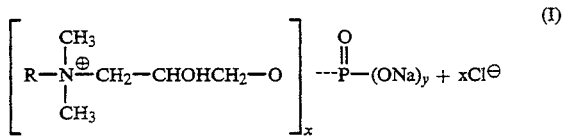

wherein R is a linoleamidopropyl or cocamidopropyl radical and x+y=3.

4. A composition according to claim 1, wherein the fatty alcohol is selected from the group consisting of myristyl alcohol or cetyl alcohol.

5. A composition according to claim 1, wherein the phospholipid is present in an amount of about 0.05 to 5% by weight of of the composition.

6. A composition according to claim 1, wherein the perfuming base is present in an amount of about to 5% by weight of the composition.

7. A composition according to claim 1, wherein the fatty alcohol is present in an amount of about 0.02 to 2% by weight of the composition.

8. A composition according to claim 1, wherein the phospholipid is present in an amount of about 0.05 to 2% by weight, the perfuming base is present in an amount of about 0.5 to 5% by weight and the fatty alcohol is present in an amount of about 0.05 to 2% by weight each weight percent calculated relative to the weight of the composition, and the composition provides an antimicrobial activity of at least 90%, as measured by the direct spray method.

9. A composition according to claim 1, wherein the perfuming base contains at least 60% by weight, relative to the weight of the perfuming base, of one or more perfuming ingredients each having an antimicrobial activity of at least 60%, as measured by the direct spray method.

10. An antimicrobial perfumed composition for inhibiting formation of perspiration odor comprising perfuming ingredients, at least 60% by weight of which have an antimicrobial activity of at least 60%, as measured by the direct spray method, a plant extract rich in flavonoids, and a suitable carrier.

11. A composition according to claim 10, wherein the plant extract is a rosemary extract.

12. A deodorant or antiperspirant article intended for body care, comprising a perfumed composition according to claim 1.

13. An article according to claim 12, in the form of a soap, a stick, a roll-on, an aerosol or a mechanical or manual pressure vaporizer.

14. A detergent or fabric softener comprising a perfumed composition according to claim 1.

15. An antimicrobial perfumed composition for inhibiting the formation of perspiration odor, comprising perfuming ingredients, at least 60% by weight of which have an antimicrobial activity of at least 60% as measured by the direct spray method, and a suitable carrier.

16. A deodorant or antiperspirant article intended for body care, containing a perfumed composition according to claim 10.

17. A deodorant or antiperspirant article intended for body care, comprising a perfumed composition according to claim 15.

18. A detergent or fabric softener comprising a perfumed composition according to claim 10.

19. A detergent or fabric softener comprising a perfumed composition according to claim 15.

20. A perfumed deodorant or antiperspirant article containing an antimicrobial composition for inhibiting formation of perspiration odor which comprises a cationic phospholipid in an amount of about 0.05 to 5% by weight, a perfuming base having an antimicrobial activity of at least about 60% as measured by the direct spray method and present in an amount of about 0.1 to 5% by weight, and a fatty alcohol having from 10 to 22 carbon atoms and present in an amount of about 0.02 to 2% by weight, wherein the cationic phospholipid is a compound of the formula

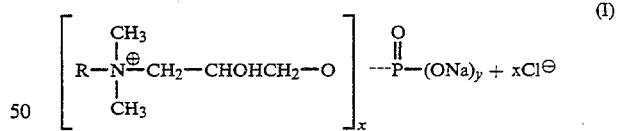

wherein R is a linoleamidopropyl or cocamidopropyl radical and x+y=3.

* * * * *